(12) United States Patent
Yamamoto

(10) Patent No.: US 7,659,098 B2
(45) Date of Patent: Feb. 9, 2010

(54) METHOD OF TREATING WASTE FROM ALCOHOL PRODUCTION

(76) Inventor: Masahiro Yamamoto, 1103, 26-1 Kamoike-Shinmachi, Kagoshima-shi, Kagoshima (JP) 890-0064

( * ) Notice: Subject to any disclaimer, the term of this patent is extended or adjusted under 35 U.S.C. 154(b) by 477 days.

(21) Appl. No.: 11/531,001

(22) Filed: Sep. 12, 2006

(65) Prior Publication Data
US 2008/0064075 A1  Mar. 13, 2008

(51) Int. Cl.
C12P 7/06 (2006.01)
C12P 7/08 (2006.01)
A61K 1/06 (2006.01)
A61K 36/899 (2006.01)
A23L 1/28 (2006.01)

(52) U.S. Cl. .................. 435/161; 424/115; 424/750; 426/46; 426/52; 426/60; 426/62; 426/592; 435/163; 435/289.1

(58) Field of Classification Search ............... None
See application file for complete search history.

(56) References Cited

U.S. PATENT DOCUMENTS

| 6,613,365 | B1 | 9/2003 | Yamamoto |
| 6,623,771 | B2 | 9/2003 | Yamamoto |
| 6,703,054 | B2 | 3/2004 | Yamamoto |
| 7,067,164 | B2 | 6/2006 | Yamamoto |
| 2006/0154353 | A1 * | 7/2006 | Duan et al. ............... 435/161 |
| 2008/0113418 | A1 * | 5/2008 | Allain et al. ............... 435/132 |

FOREIGN PATENT DOCUMENTS

| JP | 64-20090 | | 1/1989 |
| JP | 401020090 A | * | 1/1999 |
| WO | 2007/049755 | | 5/2007 |
| WO | 2007/086107 | | 8/2007 |

* cited by examiner

*Primary Examiner*—Herbert J. Lilling
(74) *Attorney, Agent, or Firm*—Pearne & Gordon LLP

(57) ABSTRACT

A method of treating a plurality of byproducts generated in the process of producing alcohol using corn as a raw material, and making effective use of them, particularly as feed compositions. The method of treating byproducts generated in the process of producing alcohol from corn comprises a step of using a koji mold to ferment a mixture of at least one solid byproduct and a distillation residue generated in the process of producing alcohol, to produce a koji fermentation product.

13 Claims, 2 Drawing Sheets

METHOD OF TREATING WASTE FROM ALCOHOL PRODUCTION

BACKGROUND OF THE INVENTION (1) Field of the Invention

The present invention relates to the treatment of waste generated in the process of producing alcohol from corn.

(2) Description of the Related Art

In recent years, the demand for biomass ethanol has increased, and an efficient method for treating ethanol production waste has been sought. Various byproducts are generated in the process of producing alcohol from corn, including corn cobs, corn fiber and distillation residues. While corn fibers have been conventionally used in livestock feeds after adding ingredients high in nutritional value such as corn steep liquor, these various byproducts have not been put to adequately effective use.

Additionally, the present applicant has proposed methods for using organic wastes such as raw garbage as feeds after fermenting them with koji mold (see U.S. Pat. No. 6,623,771 and U.S. Pat. No. 6,703,054).

BRIEF SUMMARY OF THE INVENTION

The present invention has the object of offering a method of treating a plurality of byproducts generated in the process of producing alcohol using corn as a raw material, and making effective use of them, particularly as feed compositions. That is, the present invention relates to a method of simultaneously treating solid byproducts and distillation residues generated in the process of producing alcohol using corn as the raw material. Therefore, the present invention offers a method of fermenting a mixture of koji mold with at least one solid byproduct and a distillation residue generated in the process of producing alcohol using corn as the raw material.

The solid byproducts are selected from corn cobs which are the crushed cores of corn, corn fibers generated in the process of separating starch from corn in the process of alcohol production by wet milling, and filter residues generated in the process of filtering alcohol fermentation products in the process of alcohol production by dry milling.

A first method comprises a step of mixing at least one solid byproduct selected from among corn cobs and corn fiber generating in the process of separating starch from corn, with a distillation residue generated in a distillation step, and fermenting the mixture.

A second method comprises a step of growing koji mold on a corn fiber generated in a starch separating process to produce a corn fiber koji; a step of mixing the corn fiber koji with a distillation residue generated in a distillation process; and a step of fermenting the mixture.

A third method comprises a step of mixing at least one solid byproduct selected from among corn cobs and filter residues generated in the process of filtering an alcohol fermentation product in the process of producing alcohol by dry milling, and a distillation residue generated in a distillation step, with a koji mold; and a step of fermenting said mixture.

A fourth method comprises a step of growing a koji mold on a filter residue generated in a filtration step in the process of producing alcohol by dry milling to produce a filter residue koji; and a step of mixing the filter residue koji with a distillation residue generated in a step of distilling the liquid part of a filtrate, and allowing to ferment.

Furthermore, a method is offered wherein raw materials such as distillation residues and/or solid byproducts are newly added to the koji fermentation product obtained by the above method and allowed to ferment, and this is repeated.

The koji fermentation product obtained in this way forms a feed material of good quality because distillation residues contain amino acids of good quality. Furthermore, fermentation by the koji mold enables the raw material to be broken down to smaller molecular weights, while the koji mold produces fungal proteins of good quality and secretes large quantities of digestive enzymes that are effective for digestive absorption, which are then contained in the feed material. Therefore, the feed material offered by the present invention does not need to have any nutrients specially added, and has adequate nutritional value as a feed material. The distillation residue provides energy for the heat of fermentation of the koji mold, and is thus useful for drying the byproducts. Therefore, the present invention is capable of efficiently drying and lightening the byproducts of producing alcohol, especially distillation residues, which contain moisture and therefore easily spoil, and have poor storability and transportability. Additionally, while most distillation residues have conventionally been thermally dried using fossil fuels and the like, the present invention allows them to be dried by the heat of fermentation of the koji mold, thus also contributing to reduced $CO_2$ emissions.

Additionally, it is possible to add fats and oils to the raw material of the present invention. In the present method that allows the use of oils and fats, the fermentation and heat generation can be largely increased by making use of the decomposition of the fats and oils by the koji mold, while also halting acetic acid fermentation. When fats and oils are added, the fats and oils serve as an energy source to increase the decomposition drying rate of the koji mold. Furthermore, there are few naturally occurring microbes that feed on oils and fats, thus making it possible to dominantly grow koji mold, which is relatively susceptible to contamination by other microbes.

Furthermore, the present invention relates to a plant comprising a wet milling alcohol production system that performs a step of separating starch from corn and a step of distilling an alcohol fermentation product; and a feed material production system that performs a step of growing koji mold on corn fibers generated in the starch separating step to produce a corn fiber koji, and a step of mixing said corn fiber koji with a distillation residue generated in said distillation step and further fermenting said mixture.

Additionally, the present invention relates to a plant comprising a dry milling alcohol production system that performs a step of filtering an alcohol fermentation product by separating it into a solid part and a liquid part, and a step of distilling said liquid part; and a feed material production system that performs a step of growing koji mold on said filter residue to produce a filter residue koji; and a step of mixing said filter residue koji with a distillation residue generated in the distilling step and further fermenting said mixture.

With the plants of the present invention, it is possible to simultaneously produce alcohol and a feed material, and to convert wastes generated in the process of alcohol production into dried feed materials which are easily transported, thus enabling alcohol production wastes to be efficiently treated.

DETAILED DESCRIPTION OF THE INVENTION

Herebelow, preferred embodiments of the present invention shall be described.

The present invention makes use of distillation residues and the solid parts such as corn cobs, corn fiber and/or filter residues, generated in the production of alcohol from corn, particularly the production of ethanol from corn.

"Solid byproducts" refers to corn cobs which are the crushed cores of corn, corn fiber which is generated in the process of separating starch from corn in the process of alcohol production by wet milling, and filter residues generated in the process of filtering alcohol fermentation products in the process of alcohol production by dry milling.

"Corn cobs" refer to the crushed cob portions of corn remaining after having removed the kernels.

"Corn fiber" refers to byproducts generated in the extraction of starch from corn in a method of producing alcohol by wet milling, which mainly comprises corn husks.

"Filter residue" refers to residues generated in the filtration process for separating the liquid part and solid part of an alcohol fermentation product in a method of producing alcohol by dry milling, in other words, the solid part.

"Distillation residue" refers to residues generated in the process of distillation for extracting alcohol in a method of producing alcohol by either a wet milling or dry milling. Distillation residues, particularly those generated in the production of alcohol by wet milling, normally contain as much as about 90-95 wt % water. With the method of the present invention, it is possible to concentrate the distillation residue to reduce the water content, for example, to about 80 wt %. The distillation residue can be concentrated by adding a koji mold having cellulase activity to the distillation residue and cultivating the koji mold. Due to this method, it is possible to reduce the viscosity of the distillation residue, thus accelerating the concentration and thereby making it easier to use distillation residues. An example of a koji mold having cellulase activity is *Asp. niger*, the cultivation time being, for example, about 24 hours. Additionally, the concentration can be performed by heating, and a cellulase can be added for the purpose of reducing the viscosity.

Figure 1:
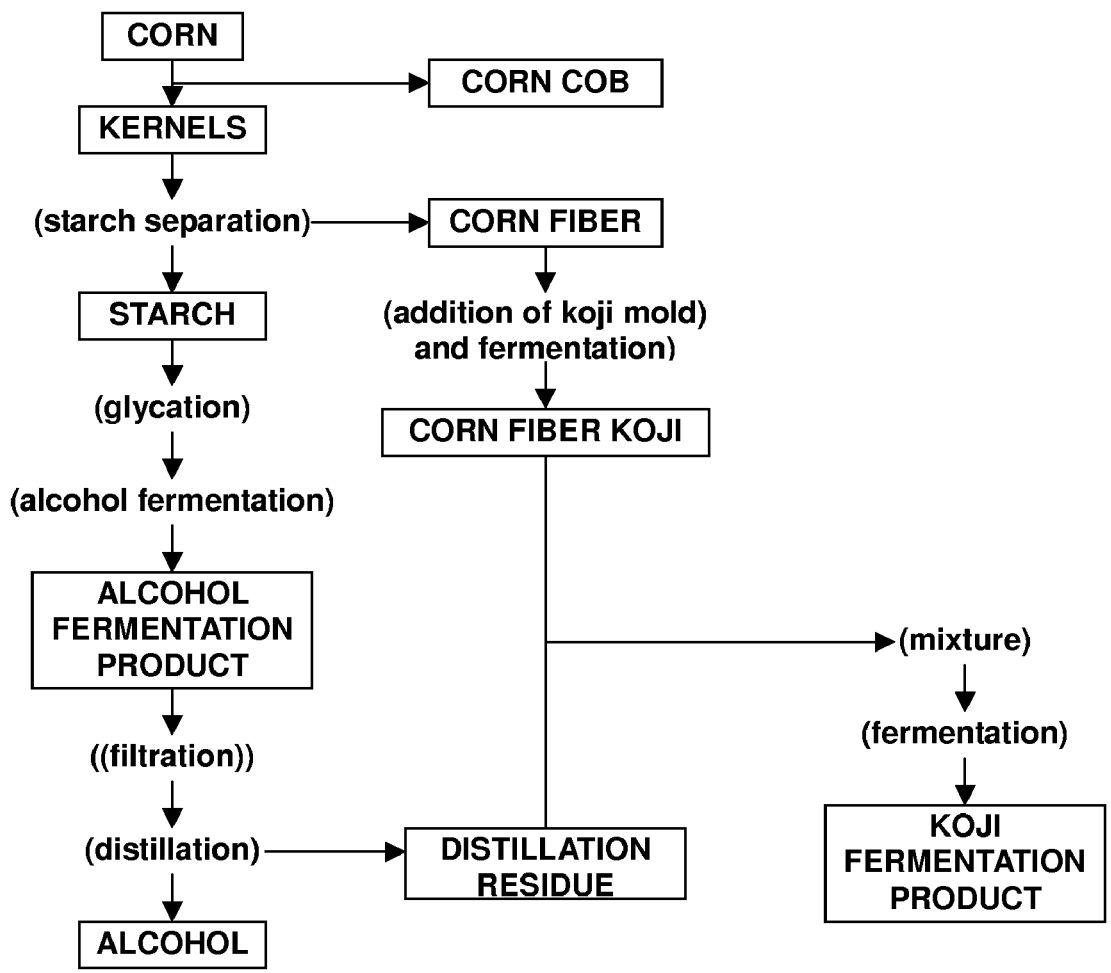
FIG. 1 is a flow chart showing a first embodiment of the present invention.

In a first embodiment of the present invention, a mixture of corn fiber and/or corn cobs with a distillation residue is fermented. This may, for example, be (1) a method of growing koji mold on corn fiber to form a corn fiber koji, mixing a distillation residue therein, and further fermenting with koji mold (see FIG. 1); (2) a method of mixing corn cobs, distillation residue and koji mold, and fermenting; (3) a method of mixing corn cobs, corn fiber, distillation residues and koji mold; or (4) a method of mixing corn cobs, corn fiber and koji mold, fermenting, then mixing in a distillation residue and further fermenting. Additionally, it is also possible to repeat the fermentation after further adding a distillation residue and/or a corn fiber.

Figure 2:
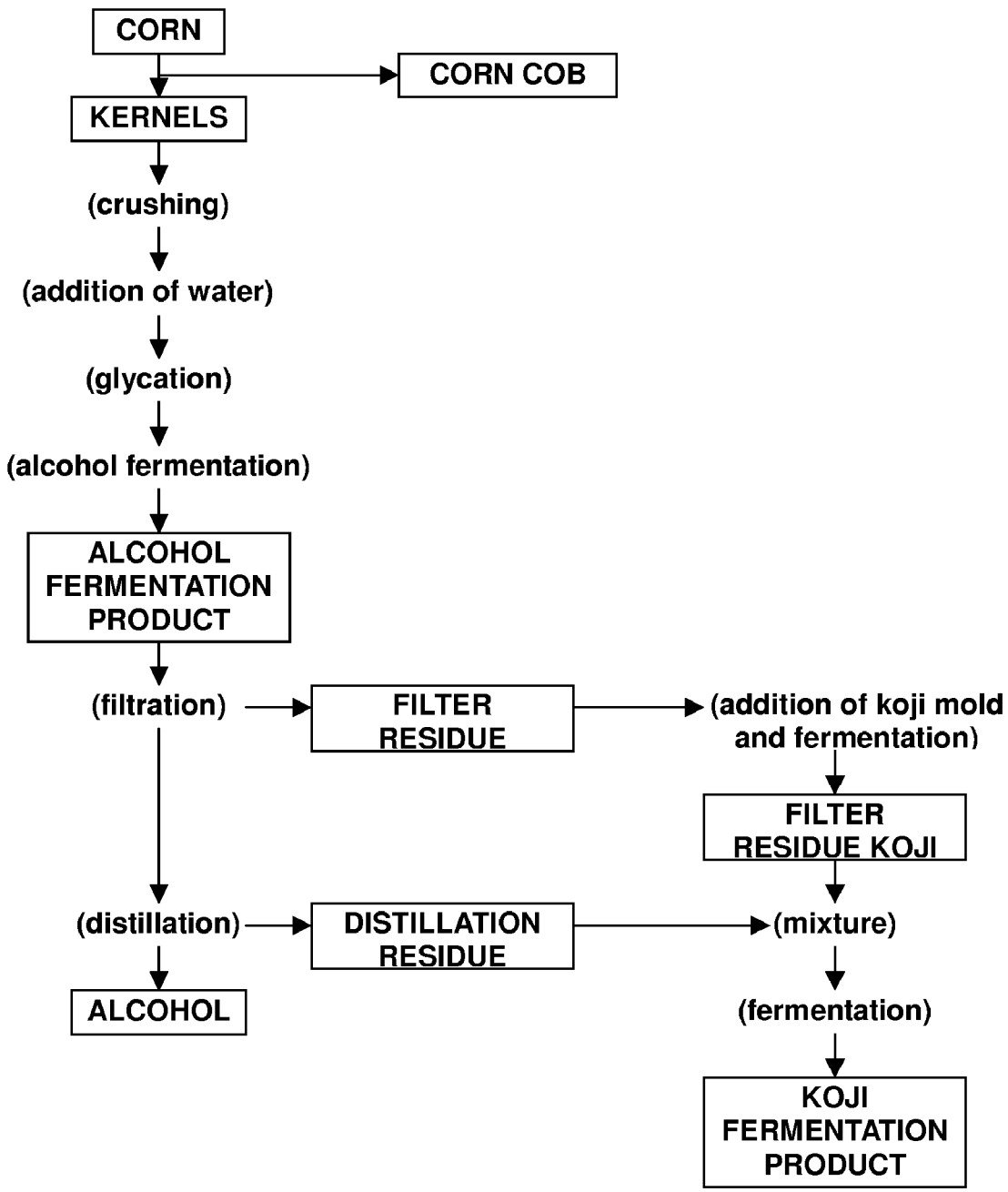
FIG. 2 is a flow chart showing a second embodiment of the present invention.

In a second embodiment of the present invention shown in FIG. 2, a mixture of filter residue and distillation reside generated in a method of producing alcohol by dry milling is fermented by koji mold. This may, for example, be (1) a method of growing koji mold on a filter residue to form a filter residue koji, mixing a distillation residue therewith, and further fermenting with koji mold (see FIG. 2); or (2) a method of mixing a filter residue, a distillation residue and a koji mold, and fermenting.

In the present invention, corn gluten may also be added as a raw material. AS a result, it is also possible to treat corn gluten which is generated in the process of producing alcohol by wet milling. Therefore, as another embodiment of the present invention, it is possible to mix corn fiber, corn cobs and koji mold and allow to ferment to form a corn fiber koji, mix this with a distillation residue, and further ferment with koji mold. Mixing corn cobs into the raw material has the effects of improving the air permeability and promoting aerobic fermentation. Therefore, the amount of the substrate needed per amount of distillation effluent to be treated is reduced when corn cobs are used as the substrate.

Additionally, the product of fermentation using corn cobs can be separated from the corn cobs, for example, by passing through a sieve. The separated fermentation product forms a feed material of high nutritional value. If fermentation is repeated by adding more alcohol fermentation residues to a fermentation product, the proteins will usually accumulate, thus raising the viscosity and generating numerous ball-shaped clusters, but when corn cobs are used, the fermentation product will not cluster, as a result of which the fermentation product can be easily separated from the corn cobs to produce a feed material that is high in proteins.

According to the method of the present invention, a feed material substantially using only corn as the raw material can be produced. In particular, the present invention has the effect of offering a feed material excelling in nutritional balance as compared with conventional feed materials formed from the byproducts of alcohol production consisting of some of the components of corn.

Each raw material is pretreated as needed in order to be usable as a raw material for a feed. This pretreatment may, for example, be sterilization. Any sterilization method may be used, but is preferably a high-temperature sterilization method, particularly steam sterilization. Steam sterilization may be for 30 minutes at about 100° C. Then, the material is preferably cooled to a temperature that is conducive to growth of koji mold, preferably 30-40° C.

The method of the present invention preferably further comprises a step of mixing an oil into the mixture. The addition of the oil enables acetic acid fermentation, to which distillation effluents are particularly susceptible, to be stopped. The amount of fats and oils normally added should be at least about 3 wt % relative to the water content of the mixture, more preferably at least about 5 wt %, and most preferably at least about 10 wt %. The fats and oils are preferably vegetable oils or animal oils, and preferably are edible oils. Furthermore, it is also possible to use waste oils such as used frying oil. The fats and oils will be digested by the koji mold and will ultimately be reduced. Furthermore, since the feed will contain lipases from the koji mold, it is possible to produce a feed material that is healthy for livestock and suitable for raising their meat quality and fattening them.

The method for treating byproducts of alcohol production of the present invention, when using oils, may be performed as follows:

i) A koji is prepared by fermenting corn fiber or filter residues by means of koji mold. Next, a distillation residue and an oil/fat is added to the koji. This mixture is fermented by the koji mold to produce a fermentation product.

ii) A distillation residue and oil are added to at least one solid byproduct selected from corn cobs, corn fiber and filter residue. A koji mold is added to this mixture to produce a fermentation product.

The water content of the raw material mixture is preferably 60 wt % or less, more preferably 50 wt % or less and even more preferably 40 wt % or less, and preferably at least 25 wt %, and more preferably at least 30 wt %. The water content of the mixture at the time of addition of the koji mold should preferably be 40-60 wt % for the purpose of causing xylanase to be produced in the fermentation product by the action of the koji mold. In order to prevent spoilage and allow for safe fermentation, the water content of the mixture at the time of addition of the koji mold should preferably be 40 wt % or less. Additionally, the corn fiber used to make the corn fiber koji should have a water content of 30-40 wt %. Furthermore, in a method of directly adding a distillation residue to corn cobs or corn fiber, the water content of the corn cobs before adding the distillation residue should preferably be 20-40 wt %, more preferably 23-35 wt %, and the water content of the corn fiber before adding the distillation residue should preferably be 15-35 wt %, more preferably 20-30 wt %. The water content may be adjusted using any method, for example, by adjusting the proportional content of the raw materials of the present invention, by drying in the sun or by heating, or by mixing in water, sawdust, wood shavings, wheat bran, rice bran, beet pulp, hay, or dried koji feed materials produced by the method of the present invention.

Additionally, a starch ingredient may further be added to the raw material, and this is particularly effective when using corn cobs which contain little starch.

Koji mold is used for the fermentation in the present invention. Examples of koji molds include *Asp. oryzae*, *Asp. awamori* and *Asp. sojae*. More specifically, *Asp. oryzae kawachii*, *Asp. awamori kawachii* (available from Kirishima Kogen Beer) are preferred. Preferably, these koji molds grow dominantly in the fermentation of the present invention. By dominantly growing these koji molds, it is possible to create an environment that is suitable for growth of the koji mold. Examples of ways to achieve this include adjusting the water content and temperature to be suitable for growth of koji mold, maintaining aerobic conditions, and adding oils to the culture.

A few hours after spreading the koji mold, the growth of the koji mold is accompanied by heat generation, thus gradually raising the product temperature. During the fermentation step, the temperature of the product should preferably be maintained in an isothermic tank or the like. A product temperature of 35-50° C. is preferable, and it can be effectively cooled by ventilation or the like. Additionally, ventilation also serves to replenish oxygen which promotes koji mold growth.

As soon as the koji mold begins to ferment, the fermentation heat causes some of the moisture to evaporate. Therefore, the feed material can be set to the required water content. The water content of the fermentation product is preferably 30 wt % or less, and more preferably 20 wt % or less.

When the fermentation advances and the water content decreases, preferably when the water content reaches about 20 wt %, a distillation residue of high water content can be further added and stirred, then the water content adjusted to about 20-45 wt %, and this can be repeated a few times, several times, or even in excess of a hundred times. In this case, a koji mold can be added as appropriate.

The fermentation product obtained by the present invention can be a feed material, particularly a feed material for livestock such as pigs, chickens and cattle. In a preferable embodiment, the feed material obtained by the present invention substantially contains only corn-derived ingredients, and is therefore easy to use and safe.

Additionally, the plant of the present invention comprises a wet milling or dry milling alcohol production system, and system for treating the waste generated by the alcohol production system.

The system for treating waste generated in the process of producing alcohol by wet milling may comprise a first tank for fermenting corn fiber by means of koji mold, and a second tank for mixing the corn fiber koji obtained in the first tank with a distillation residue and fermenting. Alternatively, the fermentation of the corn fiber and the fermentation of the distillation residue can be performed in a single tank.

The system for treating waste generated in the process of producing alcohol by dry milling may comprise a first tank for fermenting a filter residue by means of koji mold, and a second tank for mixing the filter reside koji obtained in the first tank with a distillation reside and fermenting. Alternatively, the fermentation of the filter reside and the fermentation of the distillation residue can be performed in a single tank.

EXAMPLES

Herebelow, the present invention shall be described in detail by giving examples.

Example 1

Koji mold spores ($10^8$-$10^9$ per g of culture) were added to 1 kg of sterilized corn fiber with a water content adjusted to 35 wt % and mixed well, then loaded into a stationary ventilated koji maker. Ventilation was performed to control the heat generated with the growth of the koji mold to a suitable temperature (30-50° C.). 100 hours later, the water content had decreased to 20 wt %. An ethanol distillation residue (raw material: corn) with a water content of 95% was added, and mixed well to achieve a water content of 30%. The fermentation was continued for another 24 hours in the stationary ventilated koji maker. Ventilation was performed to maintain a suitable temperature (30-50° C.). Upon reaching a water content of 20 wt %, another 150 ml of ethanol distillation residue were added, and similarly fermented. This was repeated 30 times. During this time, koji mold spores ($10^8$-$10^9$ per g of culture) were added each week. As a result, 1 kg of a fermentation product was obtained. This was fed to mice.

Example 2

Koji mold spores ($10^8$-$10^9$ per g of culture) were added to 1 kg of sterilized corn fiber with a water content adjusted to 35 wt % and mixed well, then loaded into a stationary ventilated koji maker. Ventilation was performed to control the heat generated with the growth of the koji mold to a suitable temperature (30-50° C.). 100 hours later, the water content had decreased to 20 wt %. 195 ml of an ethanol distillation residue (raw material: corn) with a water content of 80% and 6 ml of a edible waste oil were added, and mixed well to achieve a water content of 30%. The fermentation was continued for another 24 hours in the stationary ventilated koji maker. Ventilation was performed to maintain a suitable temperature (30-50° C.). Upon reaching a water content of 20 wt %, another 195 ml of ethanol distillation residue were added, and similarly fermented. This was repeated 30 times. During this time, koji mold spores ($10^8$-$10^9$ per g of culture) were added each week. As a result, 1 kg of a fermentation product was obtained. This was fed to mice.

Example 3

455 ml of ethanol distillation residue (raw material: corn) and 100 g of wheat bran were added to 1 kg of corn cobs and mixed together. Next, koji mold spores ($1.1 \times 10^{8-9}$ per g of culture) were added. A raw material mixture with the raw materials mixed together in this way was loaded into a stationary ventilated koji maker. With the growth of the koji mold, heat generation began about 12 hours after mixture of the koji mold. Ventilation was suitably performed to control this heat generation to a suitable temperature (30-50° C.). In the latter half, hot air passed through a steam heater was blown in order to achieve more efficient drying. As a result, 1 kg of a fermentation product was obtained. This was fed to pigs.

Example 4

A filter reside and a distillation residue which were the byproducts of production of alcohol by dry milling were sterilized by heat. Koji mold spores ($10^8$-$10^9$ per g of culture) were added to a mixture of 1 kg of the filter residue adjusted to a water content of 40% and 100 g of wheat bran, well mixed and loaded into a stationery ventilated koji maker. Ventilation was suitable performed to control the heat generated with the growth of the koji mold to a suitable temperature (30-50° C.). When the water content was reduced, an ethanol distillation residue was added to make the water content of the mixture about 35%. This was further fermented in the stationary ventilated koji maker. This was fed to chickens.

The invention claimed is:

1. A method of treating byproducts generated in a process of producing alcohol from corn, comprising a fermentation step of using a koji mold selected from the group consisting of *Asp. oryzae, Asp. awamori* or *Asp. Sojae*, to ferment a mixture of at least one solid byproduct selected from the group consisting of corn cobs generated in said process of producing alcohol, corn fibers generated in a process of separating starch from corn in said process of producing alcohol, and filter residue generated in a process of filtering alcohol fermentation product in said process of producing alcohol, and a distillation residue generated in said process of producing alcohol, to produce a koji fermentation product.

2. A method in accordance with claim 1, wherein the fermentation step is performed by fermenting a mixture of said corn cobs and/or said corn fiber with said distillation residue generated in the process of distilling an alcohol fermentation product.

3. A method in accordance with claim 1, wherein the process of producing alcohol comprises a step of separating starch from corn and a step of distilling an alcohol fermentation product to form said distillation residue; and the fermentation step is performed by fermenting said corn fibers generated in the starch separating step to prepare a corn fiber koji, mixing said distillation residue generated in the distillation step with said corn fiber koji, and fermenting said mixture to produce said koji fermentation product.

4. A method in accordance with claim 1, wherein the process of producing alcohol is a dry milling-process comprising a step of filtering an alcohol fermentation product to separate it into solid and liquid parts to form said filter residue and a step of distilling said liquid to form said distillation residue; and the fermenting step is performed by fermenting a mixture of said corn cobs and/or said filter residue with said distillation residue, to produce said koji fermentation product.

5. A method in accordance with claim 1, wherein the process of producing alcohol is a dry milling process comprising a step of filtering an alcohol fermentation product to separate it into solid and liquid parts to form said filter residue and a step of distilling said liquid to form said distillation residue; and the fermenting step is performed by fermenting said filter residue to produce a filter residue koji, mixing said distillation residue with said filter residue koji, and fermenting said mixture to produce said koji fermentation product.

6. A method in accordance with claim 1, wherein the koji mold is *Asp. oryzae kawachii* or *Asp. awamori kawachii*.

7. A method in accordance with claim 1, wherein the water content of the mixture prior to fermentation is 50% or less.

8. A method in accordance with claim 1, wherein all of said byproduct treated by said method consists of corn as a raw material.

9. A method in accordance with claim 1, further comprising a step of mixing an oil into the mixture.

10. A method in accordance with claim 1, further comprising a step of separating said corn cobs from the koji fermentation product.

11. A method in accordance with claim 1, comprising a step of newly adding a distillation residue to the koji fermentation product and further fermenting to produce a koji fermentation product and repeating said step once or a plurality of times.

12. A method in accordance with claim 1 or 11, wherein the distillation residue is concentrated.

13. A method in accordance with claim 12, wherein the distillation residue is concentrated by cultivating *Asp. niger* in the distillation residue.

* * * * *

UNITED STATES PATENT AND TRADEMARK OFFICE
CERTIFICATE OF CORRECTION

PATENT NO.      : 7,659,098 B2                                               Page 1 of 1
APPLICATION NO. : 11/531001
DATED           : February 9, 2010
INVENTOR(S)     : Masahiro Yamamoto It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 627 days.

Signed and Sealed this

Thirtieth Day of November, 2010

David J. Kappos
*Director of the United States Patent and Trademark Office*